US009772426B2

(12) United States Patent
Armistead, Jr. et al.

(10) Patent No.: US 9,772,426 B2
(45) Date of Patent: Sep. 26, 2017

(54) SYSTEMS AND METHODS FOR AUTOMATED, RAPID DETECTION OF HIGH-ATOMIC-NUMBER MATERIALS

(71) Applicant: Rapiscan Systems, Inc., Torrance, CA (US)

(72) Inventors: Robert A. Armistead, Jr., Los Altos Hills, CA (US); William Chang, Newark, CA (US); Edward D. Franco, San Mateo, CA (US); Joseph Bendahan, San Jose, CA (US); Jolyon A. Browne, San Jose, CA (US)

(73) Assignee: Rapiscan Systems, Inc., Torrance, CA (US)

( * ) Notice: Subject to any disclaimer, the term of this patent is extended or adjusted under 35 U.S.C. 154(b) by 869 days.

(21) Appl. No.: 14/104,625

(22) Filed: Dec. 12, 2013

(65) Prior Publication Data
US 2016/0349397 A1    Dec. 1, 2016

Related U.S. Application Data

(63) Continuation of application No. 12/780,910, filed on May 16, 2010, now Pat. No. 8,633,823.
(Continued)

(51) Int. Cl.
*G01V 5/00* (2006.01)
*G06K 9/00* (2006.01)
(Continued)

(52) U.S. Cl.
CPC .......... *G01V 5/0016* (2013.01); *G01V 5/0025* (2013.01); *G01V 5/0041* (2013.01);
(Continued)

(58) Field of Classification Search
CPC . G01V 5/0016; G06K 9/4671; G06K 2209/09
See application file for complete search history.

(56) References Cited

U.S. PATENT DOCUMENTS 5,838,758 A * 11/1998 Krug ............... G01N 23/04
378/53
6,556,653 B2    4/2003 Hussein
(Continued)

FOREIGN PATENT DOCUMENTS

WO    2011142768 A2    11/2011

OTHER PUBLICATIONS

International Search Report for PCT/US10/35048; Rapiscan Security Products, Inc.; Feb. 8, 2012.

*Primary Examiner* — Mohamed Barakat
(74) *Attorney, Agent, or Firm* — Novel IP

(57) ABSTRACT

The present invention is directed to an inspection system that has a radiation source, a detector array, an inspection region, and a processing unit, where the processing unit a) obtains a radiographic image, b) segments the radiographic image based on radiation attenuation or transmission, c) identifies at least one segmented area on the radiographic image, d) filters the at least one segmented area using at least one geometric filter, e) generates feature vectors using the filtered segmented area; and f) compares the feature vectors against predefined values to determine whether a high-atomic-number object is present.

16 Claims, 9 Drawing Sheets

Related U.S. Application Data

(60) Provisional application No. 61/178,945, filed on May 16, 2009.

(51) Int. Cl.
 *G06K 9/46* (2006.01)
 *G01N 23/04* (2006.01)

(52) U.S. Cl.
 CPC .............. *G06K 9/00* (2013.01); *G06K 9/4671* (2013.01); *G01N 23/04* (2013.01); *G06K 2209/09* (2013.01)

(56) References Cited

U.S. PATENT DOCUMENTS

| | | |
|---|---|---|
| 6,567,496 B1 | 5/2003 | Sychev |
| 6,987,833 B2 | 1/2006 | Du |
| 7,381,962 B2 | 6/2008 | Goldberg |
| 7,406,192 B2 | 7/2008 | Schmiegel |
| 7,453,987 B1 | 11/2008 | Richardson |
| 7,492,862 B2 | 2/2009 | Bendahan |
| 7,492,934 B2 | 2/2009 | Mundy |
| 7,555,099 B2 | 6/2009 | Rothschild |
| 7,750,294 B2 | 7/2010 | Bright |
| 7,809,103 B2 | 10/2010 | Du |
| 7,831,012 B2 * | 11/2010 | Foland ................... G01N 23/04 378/57 |
| 7,965,816 B2 | 6/2011 | Kravis |
| 8,116,428 B2 | 2/2012 | Gudmundson |
| 8,179,597 B2 | 5/2012 | Namba |
| 8,233,586 B1 | 7/2012 | Boas |
| 9,113,839 B2 * | 8/2015 | Morton ................... A61B 6/032 |
| 2003/0118246 A1 | 6/2003 | August |
| 2004/0017888 A1 | 1/2004 | Seppi |
| 2004/0267114 A1 * | 12/2004 | Mundy ................... A61B 6/032 600/427 |
| 2008/0037707 A1 * | 2/2008 | Rothschild ........... G01N 23/046 378/57 |
| 2008/0170655 A1 | 7/2008 | Bendahan |
| 2008/0298546 A1 * | 12/2008 | Bueno .................. G01V 5/0016 378/57 |
| 2009/0086314 A1 * | 4/2009 | Namba .............. G01N 21/6458 359/383 |
| 2010/0002834 A1 | 1/2010 | Gudmundson |
| 2010/0034353 A1 | 2/2010 | Kravis |
| 2010/0166142 A1 * | 7/2010 | Du ......................... G01N 23/09 378/53 |
| 2011/0206240 A1 * | 8/2011 | Hong ................. G06K 9/00771 382/103 |

* cited by examiner

| OBJECT | V1 | V2 | V3 | V4 |
|--------|-------|-------|-----|------|
| 373 | 15147 | 13231 | 72 | 1499 |
| 372 | 11225 | 6088 | 54 | 666 |
| 374 | 12199 | 10412 | 107 | 1537 |
| 375 | 14696 | 12036 | 111 | 847 |
| 371 | 9708 | 3524 | 27 | 651 |

FIG. 3D

SYSTEMS AND METHODS FOR AUTOMATED, RAPID DETECTION OF HIGH-ATOMIC-NUMBER MATERIALS

CROSS-REFERENCE TO RELATED APPLICATIONS

The present application relies on U.S. Provisional No. 61/178,945, filed on May 16, 2010, which is incorporated herein by reference. In addition, the present application is related to U.S. Pat. Nos. 5,638,420; 6,567,496; 6,785,357; 7,322,745; 7,368,717; and 7,526,064, which are all herein incorporated by reference in their entirety.

FIELD OF THE INVENTION

The present invention relates generally to methods for detecting specific classes of materials in radiographic images. Specifically, the materials of interest are materials that represent security threats and/or materials that may be hidden or smuggled in baggage and cargo because of their high intrinsic value, e.g. gold or platinum. More specifically, the present invention relates to systems and methods for automatically and rapidly detecting the presence of high-atomic-number (high-Z) materials such as nuclear materials; nuclear weapons; and, shielding materials that may be used to shield radiation emitted by such materials as well as by radiological dispersal devices, which can prevent them from being detected by radiation detectors. This invention also relates to the detection of other types of high-Z materials that may be smuggled in cargo due to their value, such as gold and platinum bullion, and works of art and antiquities containing high-Z materials.

BACKGROUND OF THE INVENTION

Radiographic images are produced by the detection of X-rays or gamma rays that pass through the object (e.g. the cargo in a truck or container) being inspected. The density, atomic number and the total amount of material that is present determine how much of the radiation is attenuated and, therefore, the nature and type of radiographic image produced. Thus, in addition to determining the average absorption of the X-ray or gamma-ray photons as they travel along the various X-ray paths, it is possible to derive information about the characteristics of the material. The identification of areas in the image where high-Z materials are present is of specific security interest related to the detection of certain classes of weapons of mass destruction (WMD). Radiographic images produced by conventional X-ray and gamma-ray screening systems are typically incapable of determining whether a region contains high-Z material(s). Instead, an inspector examines the image to determine if there are any areas considered suspicious due to their shape, symmetry, size, attenuation or transmittance, etc. Cargo containing suspicious areas must have the cargo contents removed for manual examination. Inspectors must make their decisions by balancing the competing objectives of trying to make certain that all actual threats are detected while maintaining a low false alarm rate to limit the amount of cargo requiring physical inspection so that the stream of commerce is not unduly impacted.

The evaluation of radiographic images by an inspector is subject to human factors that can affect threat detection. For example, threat detection has been found to vary for different inspectors due to such issues as experience, differences in innate perceptive capabilities, eye/mind fatigue from examining a large number of images, and other such hindrances.

Also, the time required to analyze a given image depends on the number of areas or objects initially deemed as being suspicious by the screening system. A typical image searching/threat detection procedure for an inspector consists of quickly reviewing the image for highly attenuating objects by looking for either high levels of attenuation or low levels of transmission. For example, any given image may contain one or more highly attenuating objects or areas that need to be examined in detail. For each object or area, the inspector manually creates contrast enhancements using an input device, such as a mouse. Each object then has to be evaluated for its total attenuation (or transmission) value whereby the inspector selects a region of interest within the object or area and estimates the average pixel value which reflects the total attenuation (or transmission) of the X rays or gamma rays along that path. Before the net attenuation (or transmission) of the object can be estimated, the attenuation (or transmission) of the surrounding background materials has to be analyzed. Then, to generate an estimated net attenuation (or transmission) of the object, the background must be subtracted from the total attenuation. Finally, the inspector must examine the shape and size of the object, and combine these estimates with the estimated net attenuation (or transmission) to reach a conclusion of whether the object represents a threat. This procedure would typically have to be repeated for each suspicious object or area within an image. If done accurately, this is a very time-intensive procedure.

For example, U.S. Pat. No. 7,366,282, assigned to Rapiscan Systems, Inc. and incorporated herein by reference, is "directed towards a method for identifying an object concealed within a container, comprising the steps of generating a first set of data using a first stage X-ray inspection system; processing said first set of data using a plurality of processors in data communication with the first stage inspection system; identifying at least one target region from said processed first set of data; positioning an inspection region relative to the target region wherein the inspection region at least partially physically coincides with the target region; generating the inspection region through a second stage inspection system; and producing a second set of data having a X-ray signature characteristic and fluorescence signature characteristic of the material in the inspection region." Further, "[i]n another embodiment, the present invention comprises a single stage inspection system comprising an X-ray diffraction and fluorescence system. Contraband, high-Z or other illegal material located within a target object is identified using a radiation source by passing a target object into a C-shaped inspection system; directing an X-ray beam from said radiation source toward a target object; detecting a diffraction signal using a diffraction detector head; detecting a fluorescence signal using a fluorescence detector head; and identifying contraband material using said diffraction signal and said fluorescence signal. The method can further comprise the steps of: generating an image of said target object; analyzing the image using an algorithm to evaluate regions of objects based upon a threshold level; segmenting said image into regions based upon criteria; further inspecting selected regions satisfying certain criteria to determine their size and shape; comparing said selected regions to threat criteria; and issuing an alarm to an inspector when an object is determined as matching said threat criteria in said comparing step."

In another example, U.S. Pat. No. 6,347,132, assigned to AnnisTech, Inc. and incorporated herein by reference, discloses "an executable routine 50 for automatically detecting nuclear weapons materials. This routine is preferably executed by the signal processor and controller 28 (FIG. 1). Step 52 is performed to sample each of the individual detector elements of the transmission detector 22 (FIG. 1) as the object under inspection 12 (FIG. 1) is scanned relative to the fan beam 20 (FIG. 1), and digitize and store the sampled values. Test 54 performs a threshold detection on the sampled values to identify any areas of unusually high absorption within the image of the object under inspection. That is, since the nuclear weapons materials absorb x-rays significantly more than any other materials, the magnitude of the sampled signals associated with areas within the object under inspection having nuclear weapons materials will be significantly different than the surrounding areas. Therefore, threshold detection is a suitable automatic detection technique. Alternatively, spatial frequency analysis may also be used to detect large changes in the sampled signal magnitude, which may then be analyzed to determine whether or not the large changes in magnitude are consistent with nuclear weapons materials. In any event, detection of the nuclear weapons materials is automatic. Similarly, the region of high attenuation identified in the transmission image is examined in the scatter image (if the pencil beam system is employed). A negative result in the scatter image reinforces the result from the transmission beam analysis. If nuclear weapons' materials are detected, step 56 provides a warning annunciator that may be displayed on the display, initiates an audio alarm, or provides other suitable warning devices."

In yet another example, U.S. Pat. No. 7,492,682, assigned to GE Homeland Protection, Inc. describes "[a] method for inspecting a container for contraband, said method comprising: positioning the container on a platform configured to support the container, the platform rotatably coupled to a frame that is movably coupled to a base defining an axis, the frame movable with respect to the base in a direction parallel to the axis, and the platform movable with the frame and rotatable with respect to the frame about the axis; producing X-ray beams having at least one energy distribution and transmitting the X-ray beams through the container as the container rotates about the axis and moves in a direction parallel to the axis; detecting the X-ray beams transmitted through the container with an array of detectors to generate signals representative of the detected radiation; and processing the signals to produce images of the container and contents of the container to generate a map for the container including at least one of a CT number, a density and an atomic number corresponding to the contents within the container."

Conventional prior art threat detection uses various techniques such as conventional radiography, dual-energy imaging, resonant absorption/fluorescence, computed tomography (CT) systems, dual-stage X-ray diffraction and fluorescence systems, to produce radiographic images that are either inspected manually for threat detection and/or analyzed using software routines.

For example, high-energy dual-energy techniques have been employed in conventional systems. Multi-energy inspection employs scanning large objects with two or more energies in the megavoltage region, i.e. 6 MV and 9 MV. This technique is based on the difference of the X-ray attenuation for materials with different atomic numbers. Collecting transmission information for multiple energies enables determining the atomic number of a material along the X-ray path length.

U.S. Pat. No. 7,483,511, assigned to GE Homeland Protection, Inc. describes "[a] method of determining a presence of items of interest within a cargo container, the method comprising: obtaining information from an initial radiation scan of at least one of the cargo container and contents therein, the obtaining comprising: transmitting a screening radiation beam along a screening portion of the cargo container at a screening scan rate; detecting radiation received in response to the transmitting the screening radiation beam; and analyzing the detected radiation received in response to the transmitting the screening radiation beam to develop information regarding the initial radiation scan; identifying a target portion of the cargo container in response to the information obtained, wherein the screening portion is larger than the target portion; transmitting a target radiation beam along the target portion of the cargo container at a target scan rate, the target scan rate being different than the screening scan rate; detecting radiation received in response to the transmitting; analyzing the detected radiation for a presence of items of interest; and in response to the analyzing, generating a first signal indicative of the presence of the items of interest, or generating a second signal indicative of an absence of the items of interest."

Further, U.S. Pat. No. 7,286,638, assigned to Passport Systems, Inc. describes "[a] method for analyzing material in a voxel of a target, the method comprising: illuminating the voxel with a photon beam; measuring a first number of photons scattered from the voxel in a first energy range and in a first measurement direction; measuring a second number of photons scattered from the voxel in a second energy range and in a second measurement direction; determining a ratio of the first number of photons to the second number of photons; determining an average atomic number of the material in the voxel using the ratio; and generating a signal based upon the average atomic number determined."

And still further, United States Patent Publication Number 20090323889 describes a "[s]ystem and method for XRD-based false alarm resolution in computed tomography ("CT") threat detection systems. Following a scan of an object with a megavoltage CT-based threat detection system, a suspicious area in the object is identified. The three dimensional position of the suspicious area is used to determine a ray path for the XRD-based threat detection system that provides minimal X-ray attenuation. The object is then positioned for XRD scanning of the suspicious area along this determined ray path. The XRD-based threat detection system is configured to detect high density metals ("HDMs") as well as shielded Special Nuclear Materials ("SNMs") based on cubic or non-cubic diffraction profiles."

The prior art, however, suffers from severe limitations for the high-throughput inspection of large dense cargo. For example, inspection methods based on dual-energy and fluorescent methods have difficulties with threat detection within dense, highly attenuating cargo; CT systems are not practical for inspection large cargo because of size and speed constraints. Further, software routines based on threshold detection have not proven effective due to the inability to distinguish between the presence of high-Z materials and areas that have high attenuation due to their thickness and density.

What is therefore needed is a method for automatically and rapidly analyzing radiographic images, specifically for high-atomic-number (high-Z) materials, where "high-Z" refers to materials in the periodic table of atomic number 72 (Hafnium) and above.

What is also needed is a method for accurately detecting high-Z materials in very large and dense objects (e.g. containers containing metals and other dense cargo) with an inspection and analysis speed that results in minimal additional delay in the clearing of cargo.

What is also needed is a method that implements complementary modules that analyze the radiographic image using both threshold and gradient detection techniques along with characteristic geometric and physical considerations to reduce false alarms while automatically and rapidly rendering "High-Z"/"Clear" decisions.

SUMMARY OF THE INVENTION

In one embodiment, the present invention is directed toward an inspection system comprising: a radiation source; a detector array; an inspection region bounded by said radiation source and detector array; a processing unit, wherein, through operation of at least one processor, at least one memory, and programmatic instructions, said processing unit obtains data representative of a radiographic image; segments said data based on radiation attenuation or transmission; identifies at least one segmented area within said data representative of said radiographic image; filters said at least one segmented area using at least one geometric filter; generates a plurality of feature vectors using said filtered segmented area; and compares said feature vectors against predefined values to determine whether a high-atomic-number object is present.

Optionally, the radiographic image has a spatial resolution of at least 0.25% of a minimum size of a threat object. The radiation source is at least one of X-ray or gamma-ray radiation. The processing unit generates a map of said segmented data representative of said radiographic image by determining local maximum peak attenuation values. The processing unit generates a map of said segmented data representative of said radiographic image by determining minimum transmission values and applying edge gradient calculations. The geometric filter is at least one of shape, symmetry, size or homogeneity. The size filter is applied to at least one segmented area to identify dimensions selected on the basis of spatial resolution or penetration. The shape filter is applied to at least one segmented area to identify a spatial aspect ratio of less than 20. The segmented area has a first number of pixels and wherein a second defined area has a second number of pixels and wherein the homogeneity filter is applied to determine a ratio of said first number of pixels to said second number of pixels.

Optionally, the processing unit generates a plurality of feature vectors using said filtered segmented area by: obtaining an image of said filtered segmented area; estimating background attenuation around said filtered segmented area; subtracting the background attenuation from said filtered segmented area to generate a net attenuation of the filtered segmented area; estimating dimensions of the area of interest using said net attenuation of the filtered segmented area; calculating an attenuation of the filtered segmented area as if it were a high-Z material; and comparing the calculated attenuation of the filtered segmented area of interest to the net attenuation of the filtered segmented area.

Optionally, the feature vectors comprise at least one of maximum attenuation, net attenuation, a ratio of attenuation to an area of a suspicious object, a gradient of a suspicious object along a boundary, and a difference produced between measured background corrected attenuation and calculated attenuation. The feature vectors are compared against predefined values to determine whether a high-atomic-number object is present.

In another embodiment, the present invention comprises an inspection system comprising a processing unit, wherein said processing unit: segments data of a first radiographic image, which is representative of a first view of an object, and a second radiographic image, which is representative of a second view of the object, based on radiation attenuation or transmission; filters at least one segmented area using at least one filter for each of said images; generates a plurality of feature vectors using said filtered segmented area for each of said images; and determines whether a high-atomic-number object is present using said feature vectors for each of said images.

Optionally, each of said radiographic images is produced using at least one of an X-ray or gamma-ray radiation source. The processing unit activates an alarm if each of said images indicates the presence of a high atomic number object. The filter is at least one of shape, symmetry, size or homogeneity. The size filter filters said at least one segmented area to identify dimensions selected on the basis of the inspection system's spatial resolution or penetration. The shape filter filters said at least one segmented area to identify a spatial aspect ratio of less than 20.

In another embodiment, the present invention is an inspection system comprising a processing unit, wherein said processing unit: segments data of a first radiographic image, which is representative of an object and generated at a first energy level, and a second radiographic image, which is representative of the object and generated at a second energy level; filters at least one segmented area using at least one filter for each of said images; generates a plurality of feature vectors using said filtered segmented area for each of said images; performs a ratio operation on said plurality of feature vectors, resulting in a ratio feature vector; and determines whether a high-atomic-number object is present using said ratio feature vector. The processing unit activates an alarm if each of said images indicates the presence of a high atomic number object.

BRIEF DESCRIPTION OF THE DRAWINGS

These and other features and advantages of the present invention will be appreciated, as they become better understood by reference to the following detailed description when considered in connection with the accompanying drawings wherein:

FIG. 3D is a feature vector table used in the present invention that contains representative values;

DETAILED DESCRIPTION OF THE DRAWINGS

Figure 1:
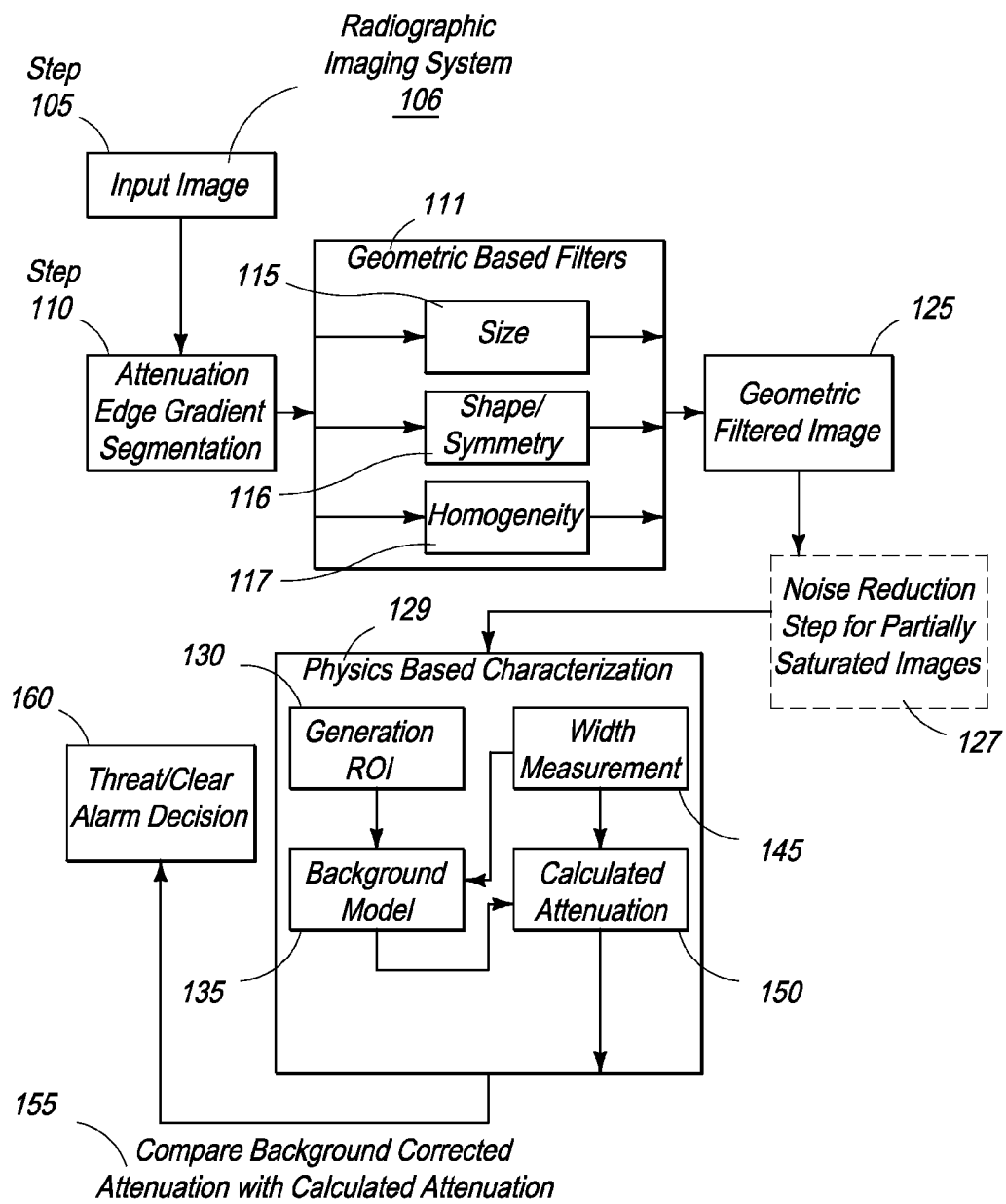
FIG. 1 is a block diagram illustrating steps of one embodiment of a radiography-based method of the present invention for automatically and rapidly detecting the presence of high atomic-number (high-Z) materials from a conventional radiographic image.

The present invention is directed towards methods for detecting specific classes of materials (i.e. high-Z) within radiographic images. More particularly, the present invention is directed towards a threat detection method for automatically and rapidly analyzing radiographic (X-ray, gamma-ray, etc.) images of cargo, such as crates, trucks, sea containers, baggage, and other cargo, for security threats and other types of contraband, in particular, high-atomic-number (high-Z) materials. Thus, in one embodiment, the present invention is directed towards increasing screening throughput and eliminating the need for an inspector or security screening system operator to manually examine suspicious areas within the radiographic image.

For purposes of this invention, "high-Z" refers to materials in the periodic table of atomic number 72 (Hafnium) and above, with the exception of Polonium (84) which, due to its very low density, falls outside of the effective range of the methods of the present invention.

In one embodiment, the present invention is directed towards a contraband detection method that efficiently detects high-Z materials, such as, but not limited to, special nuclear material(s) (SNM) (i.e. uranium, plutonium) in an assembled nuclear device; a separate quantity of SNM intended for the eventual assembly into a nuclear device; and, one of a number of high-Z materials (e.g. tungsten, lead) typically used to shield radioactive materials to prevent the emitted radiation from being detected by the arrays of passive detectors that are being placed into operation at a number of global ports of entry. Examples of radiation-emitting threats include SNM and radioactive isotopes that could be used in a radiological dispersal device (i.e., "dirty bomb"). The present invention also provides a method for detecting other types of contraband including high-Z materials of high value, such as gold and platinum, and art objects containing high-Z materials.

The threat detection methods of the present invention advantageously use physical properties such as material density, mass absorption coefficient, and dimension. In one embodiment, the threat detection method of the present invention requires a much shorter analysis time and, thus, allows for higher system throughput. The time to analyze a given radiographic image depends on the number of objects selected as being suspicious during the analysis.

In a conventional system, a typical procedure consists of an inspector manually reviewing the image for objects that are highly attenuating. For example, if multiple objects that are highly attenuating are identified, the inspector would need to make contrast enhancements with each object using a computer and input device, such as mouse. Each object has to then be evaluated for its total attenuation (or transmission) value by using the computer to select a region of interest within the object and making an estimate of the average attenuation (or transmission) value, which reflects the total attenuation (or transmission) along the X-ray path through the cargo. Before the net attenuation (or transmission) of the object can be estimated, the attenuation (or transmission) of the surrounding background materials has to be analyzed. Then, to generate an average net attenuation (or transmission) of the object, the background must be subtracted from the total attenuation (or added to the transmission). Finally, the inspector must examine the shape and size of the object, and combine these estimates with the estimated net attenuation (or transmission) to reach a conclusion of whether the object represents a threat. This procedure would have to be repeated for each object and, therefore, if performed accurately, would be a very time-intensive procedure.

Figure 2:
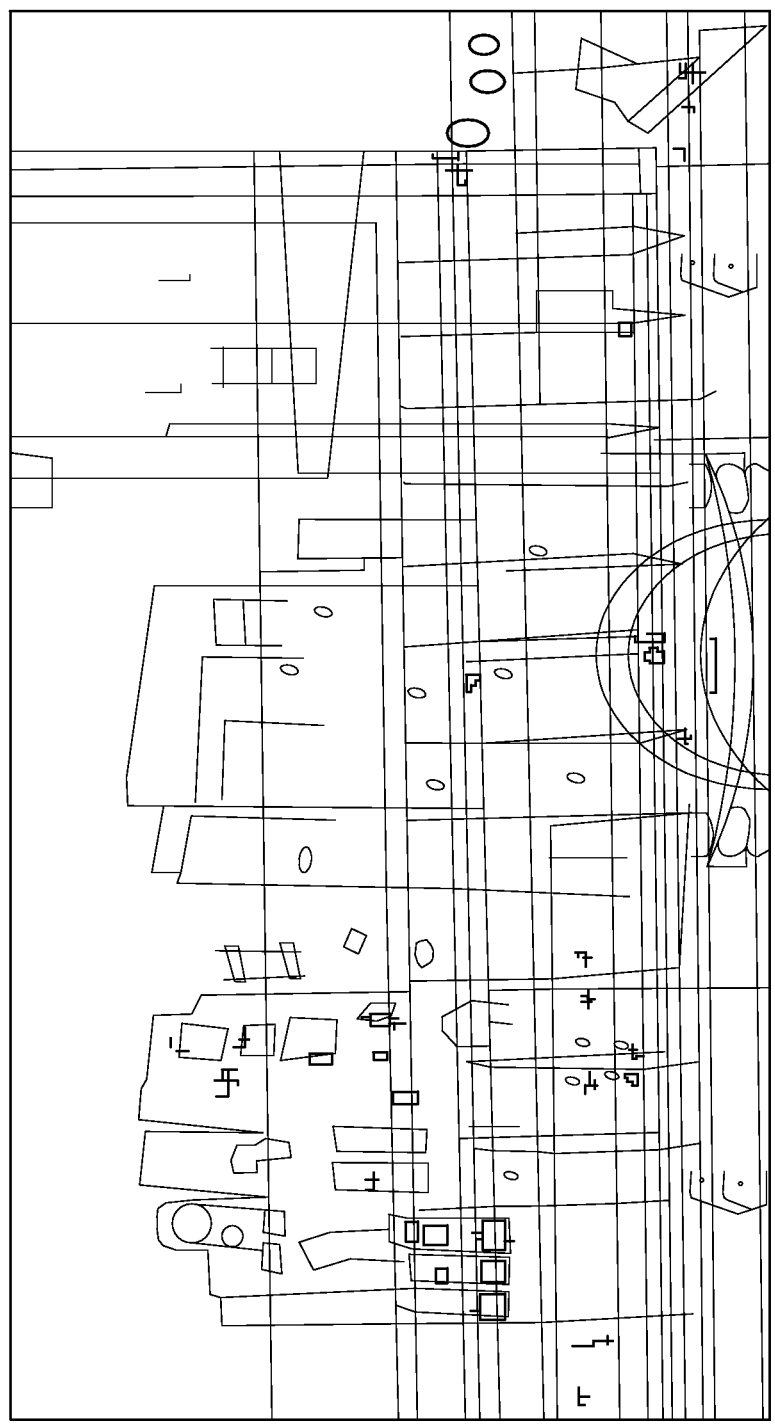
FIG. 2 is an illustration of a conventional X-ray radiographic image showing the attenuation produced by the contents of a cargo container.

In using the threat detection methods of the present invention, however, the decision time ranges from typically less than one second for cargo determined not to have any suspicious objects, to less than approximately 5 seconds for cargo such as the image shown in FIG. 2 having a plurality of objects or areas of interest, depending upon the processing speed of the computer that is used. In other embodiments of the present invention, as described below, decision processing time may increase or decrease, depending upon the complexity of the cargo and/or scan.

In prior art methods, threat detection has been found to vary for different inspectors due to such issues such as experience, differences in innate perceptive capabilities, eye/mind fatigue from examining a large number of images, among other factors. Thus, in addition to image analysis speed, the threat detection methods of the present invention are advantageous in that they are capable of performing a consistent analysis using the same physical principles and decision criteria for all images. Thus, threat detection is made less susceptible to human factors that can affect the analysis of radiographic images by an inspector. Further, automated detection using the present invention is advantageous for detecting threats within partially saturated areas (i.e. areas not fully penetrated by the X-ray beam). Because of the statistical uncertainty in the attenuation or transmission values of partially saturated regions, much more elaborate manual procedures would be required in order for an inspector to analyze these regions and subsequently make a decision.

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that are known in the technical fields related to the invention have not been described in detail so as not to unnecessarily obscure the present invention.

In addition, one of ordinary skill in the art would appreciate that the features described in the present application can operate on any computing platform including, but not limited to: a laptop or tablet computer; personal computer; personal data assistant; cell phone; server; embedded processor; main-frame, DSP chip or specialized imaging device. Additionally, the programmatic code can be compiled (either pre-compiled or compiled "just-in-time") into a single application executing on a single computer, or distributed among several different computers operating locally or remotely to each other. It should further be appreciated that all of the method steps disclosed herein, including any and all processing or analytical functions, are implemented in such programmatic code stored in a memory and executed on by at least one processor in the computing platform.

In one embodiment, the threat detection methods of the present invention operate by first receiving, on a computing platform, a radiographic image of an object from an X-ray imaging system which typically comprises a radiation source positioned opposite to, or away from, a detector array. At least part of the area bounded by the radiation source and detector array is an inspection region, through which the cargo being inspected passes, or is positioned. Exemplary X-ray imaging systems are shown in U.S. Pat. Nos. 5,638,420; 6,567,496; 6,785,357; 7,322,745; 7,368,717; and 7,526,064, which are all herein incorporated by reference in their entirety. It should be noted that the software application of the present invention can be used with any X-ray or gamma-ray imaging system that includes a computing platform. In one embodiment, the screening system acquires the original image, which is then processed by the methods of the present invention.

The X-ray imaging system is in electrical communication, either wired or wirelessly, with the computing platform. The threat detection methods then perform a first level analysis to generate a first "suspicious object" binary map by measuring a number of physical attributes. Each area on the initial binary map is used as a mask to electronically crop out part of the X-ray radiographic image for analysis, including its surrounding background attenuation (or transmission) and physical characteristics such as attenuation, size, and shape. Then, a decision is made of whether that area or portion could represent a high-Z object. This decision process results in a second binary map, which highlights those regions that represent potential high-Z threats.

While described with respect to its use in an X-ray imaging system, it should be noted that the threat detection methods of the present invention can be used with X-ray and gamma-ray sources of various energies and intensities, whereby a sufficient amount of radiation (X rays or gamma rays) penetrates the object under inspection so as to produce measurable signals in the detector above noise levels. Therefore, the required source energy and intensity is dependent on the physical dimension of the cargo along the direction of the X rays and the composition of the cargo, such as its density and atomic number. Further, the methods of the present invention can be used with X-ray or gamma-ray beams that are constant in intensity or where the intensity or energy is modulated. Still further, the present invention can be used with systems that employ radiation beams that vary in energy or with systems that produce radiation of different energy or with systems that use a low-energy detector in-line with a high-energy detector, including, but not limited to dual-energy and multi-energy radiographic imaging systems.

FIG. 1 is a block diagram illustrating steps of a radiographic imaging method of the present invention for automatically and rapidly detecting the presence of high-Z materials. In one embodiment, the threat detection methods of the present invention, in step 105, receives a radiographic image from an imaging system 106, such as an X-ray imaging system. An exemplary radiographic image 200, of a cargo container, is shown in FIG. 2, showing objects within the cargo container.

The capability of the methods of the present invention to detect specific high-Z materials and the alarm rate associated therewith is dependent upon image quality. Thus, the imaging system of the present invention should have sufficient spatial resolution so that it is able to resolve high-Z objects. In one embodiment, a spatial resolution that is approximately 25% of the minimum size of the high-Z object to be detected is adequate. For example, if the minimum size of the high-Z object is 1 inch, then the spatial resolution of the imaging system should be at least 0.25 inches. For systems with poorer resolution, the probability of detection and the false alarm rate can be adversely affected. The detection of a high-Z object is not strongly dependent on the contrast resolution of the image unless areas of the image are partially saturated; in such cases, high contrast resolution is advantageous.

Other factors can also affect the image quality and, hence, the successful detection of threats. Under some conditions, image artifacts can result from the specific design of the imaging system. For example, the presence of structural components of the cargo container, such as the metal ribs present in sea cargo containers, can affect the accuracy of the methods of the present invention. These ribs may be present in the radiographic image as narrow vertical lines that may complicate the ability to segment high-Z objects if they appear in the image at the location of a suspicious area with high attenuation or low transmission. Since the methods disclosed herein can be used with virtually any type of X-ray imaging system, the extent of any image artifacts will be system and cargo container dependent. Thus, image and signal processing techniques, determined on a case-by-case basis, would be needed to minimize artifacts.

Referring back to FIG. 1, the radiographic image 106 serves as the input to the threat detection methods of the present invention. The image 106 is subsequently segmented in step 110, based on the X-ray attenuation (or transmission) of the object. X-ray attenuation of an object is material-dependent, and is governed by the following equation for X-ray or gamma-ray radiation at a nominal energy, E:

$$\frac{I(E)}{I_o(E)} = e^{-\mu(E)t} \qquad \text{EQUATION 1}$$

where μ is the linear attenuation coefficient and t is the X-ray beam path length through the object Accordingly, by knowing, detecting, measuring, or determining the X-ray input, output, and beam path length, one can determine the linear attenuation coefficient, which is indicative of the material being scanned. In one embodiment, during the image segmentation process of step 110, the edge gradients of the objects in the image are employed to identify potential high-Z areas in the presence of a highly cluttered background, produced by complex cargo with high-spatial frequencies. This is effective since a high-Z object will produce a high attenuation value or low transmission value in the radiographic image and will also have a large attenuation or transmission gradient along its edges.

The image segmentation is performed by using a processor that loads from a memory device (hard disk, RAM, ROM, RAID array, flash drive, USB device, or other memory) the data representative of the radiographic image and that subjects the data to a program which performs the image segmentation calculations as described herein.

Figure 3A:
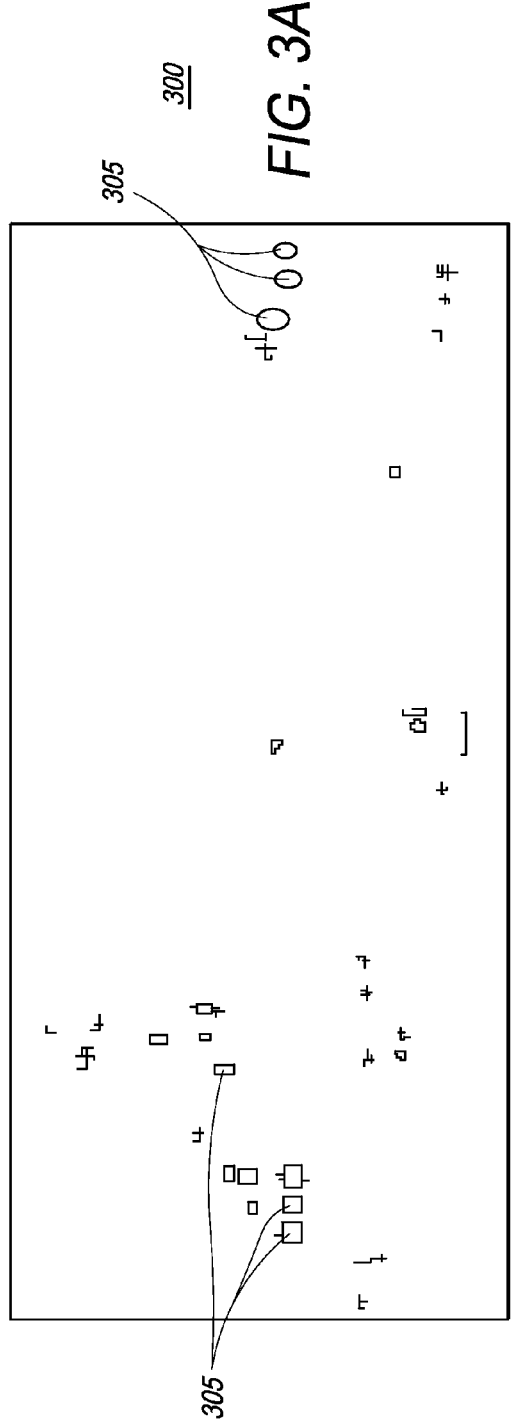
FIG. 3A is an initial segmented map of suspicious objects or areas for further analysis of the X-ray radiographic image of FIG. 2, using the present invention.

The image segmentation performed in step 110 results in an initial map of potential high-Z objects or areas by determining local maximum attenuation (or minimum transmission) values with multi-threshold segmentation. Alternatively, the initial map of potential high-Z objects or areas can be generated by determining local minimum transmission values with multi-threshold segmentation. FIG. 3A is an initial segmented map 300 of the radiographic image shown in FIG. 2 showing potential high-Z objects or areas based on local maximum attenuation 305 that would need further analysis.

Referring back to FIG. 1, next, in a geometric-based module 111, a plurality of filters are applied to the segmented radiographic image to reduce the number of segmented areas for further analysis by applying geometric constraints. In one embodiment, the geometric constraints applied are predetermined metes and bounds in terms of shape, symmetry, size and homogeneity. The filters are applied by using a processor that loads from a memory device (hard disk, RAM, ROM, RAID array, flash drive, USB device, or other memory) the data representative of the segmented images of the radiographic image and that subjects the data to a program which performs size, shape, and homogeneity calculations, as described herein.

In one embodiment, in step 115, a size filter excludes regions that are either smaller than the minimum size of objects to be detected or larger than the size of an object through which the penetration of the radiation beam becomes insufficient. The method of the present invention can be employed with radiographic systems of various energies and performance capabilities ranging from high-resolution, low-penetration baggage inspection systems to lower resolution, but higher penetration systems designed for the inspection of dense cargo carried in trucks, sea containers, and other dense cargo. In selecting the dimensions to be used in the methods of the present invention, consideration should be given to the performance of the radiographic system that is acquiring the image data, in particular, the system's spatial resolution and penetration. Generally, the smallest size of the object to be detected should be set to a value that is approximately four times greater than the system's spatial resolution; the larger size dimension should be one for which reasonable detector signal-to-noise levels are achieved (on the order of a signal to noise ratio of 3 to 1) and limited image saturation occurs. For example, the Rapiscan Systems' Eagle™ Portal, a 6 MV cargo imaging system, achieves a spatial resolution of 0.25 inches and a penetration limit of 425 mm of steel. Thus, the minimum size of the high-Z object would be 1 inch (4 times greater than the spatial resolution) and the maximum size would be approximately 400 mm of steel. Although the dimensions can be set to different values, the competing interests of both the penetration and resolution of the system must be considered since, in combination, they largely determine the probability of detection and the false alarm rates that are experienced during operation. In the case of insufficient penetration, the segmented object or area is labeled with a bounding box for the inspector.

In step 116, a shape filter eliminates objects with an aspect ratio greater than a pre-determined, pre-set value and retains objects with common primitive shapes, such as cubes, cylinders and spheres. In one embodiment, the pre-determined aspect ratio is set between 4 and 20. The aspect ratio of the object is derived by calculating the ratio of the lengths of the major axis to the minor axis of the object. Thus, in one embodiment, in applying the shape filter of the present invention, any object having an aspect ratio of greater than 20 is discarded. For more complex shapes, namely, a combination of primitive shapes, a symmetry feature is used for shape determination. The symmetry analysis is applied to at least one segmented area to characterize the two-dimensional boundary of the area as a one-dimensional function of the polar angle from the centroid of the segmented area. This one-dimensional function is analyzed to quantify the shape of the segmented area and its degree of symmetry through the magnitude and periodicity of the function. As an example, the symmetry filter may be generated through radial Fourier expansion and other techniques that are known to those skilled in the art of automated characterization of shapes through machine vision.

In step 117, a homogeneity filter rejects any regions that contain patterns of scattered clusters of pixels connected by only a few pixels. In one embodiment, the homogeneity filter is defined by the ratio of the number of the pixels in the segmented area to the number of pixels contained in a bounding box around the segmented area. In one embodiment, the predetermined homogeneity filter is set between 40% and 80%, depending on the desired sensitivity. In one embodiment, the predetermined minimum ratio of the homogeneity filter is set at 50%. Thus, in applying this predetermined homogeneity filter, any regions where the ratio of the number of the pixels in the segmented area to the number of pixels contained in a bounding box around the segmented area is less than 50% are discarded. While different ratio values can be employed, the use of small ratios can contribute to a larger number of false positives.

Optionally, additional filters may also be applied to potential high-Z object areas in the radiographic image. These include the use of texture to identify areas for further analysis as a potential high-Z object and symmetry filters that could be used to identify shell-like high-Z objects and establish a shape or boundary vector. The boundary vector can then be compared to predetermined boundary vectors on the basis of shape, which is invariant to translation, rotation and scaling, and predetermined geometrical landmarks that describe a particular high-Z object of interest. Other geometrical filters may include form factor, which is a measure of the elongation of the object, roundness, and compactness. Some filters designed for removal of certain image artifacts, such as directional streak filters and noise smoothing filters, could also be applied in conjunction with geometric filters, when there are artifacts present. Additionally, the filters can be used in parallel or serially.

In step 125, the resultant geometric-filtered image, comprising at least one potential high-Z area, is communicated to a characterization module 129 to analyze each region within the image map and generate a feature matrix, which includes the outputs of all the functions within the characterization module, for ultimate decision analysis. Within the characterization module 129, the region of interest (ROI) around each suspicious area is obtained in step 130, by cropping the radiographic image using the object map as a mask. The characterization module 129 is applied by using a processor that loads from a memory device (hard disk, RAM, ROM, RAID array, flash drive, USB device, or other memory) the data representative of the filtered images of the radiographic image and that subjects the data to a program which performs the vector analyses described herein.

Figure 3B:
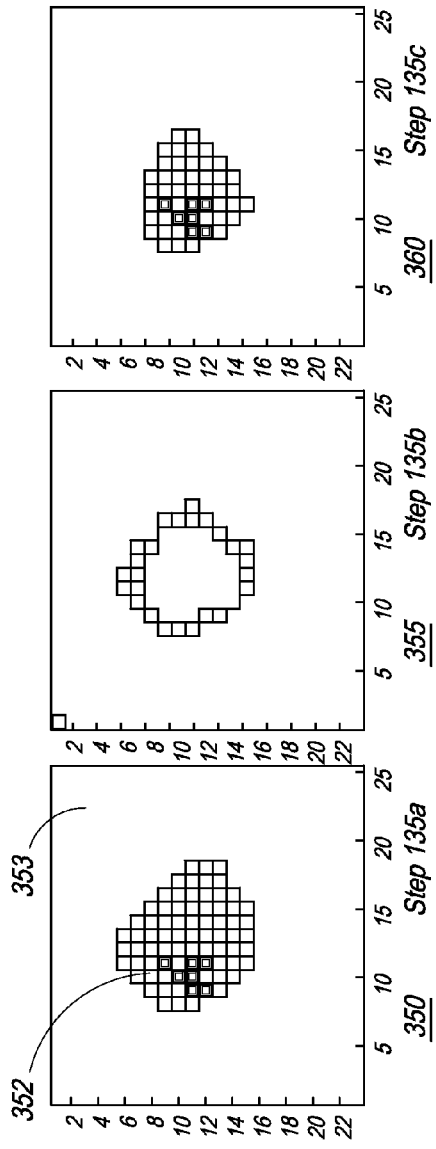
FIG. 3B is an illustration of at least one model used to estimate the background around the object of interest, using the present invention.

In step 135, at least one model is used to estimate the background around the object of interest. FIG. 3B is an illustration of the background estimation model used to estimate the background around the object of interest in one embodiment of the present invention. As shown in FIG. 3B, in step 135a, image 350 is created as object 352 is superimposed on top of a non-uniform background 353, which is selected by enlarging the region of interest symmetrically by an amount dependent on the original size of the region of interest and the spatial frequency of the surrounding cargo. In step 135b, the background function then estimates the attenuation (or transmission) of the background objects by using the surrounding attenuation information to linearly fit the attenuation pixel by pixel within the region of interest, as shown in image 355. In step 135c, the background attenuation derived in step 135b (or image 355) is subtracted from the original image 350. The resultant image 360 is the net attenuation due to the object.

The dimensions (such as width, for example) of the object are estimated at step 145. In one embodiment, this estimation is performed substantially simultaneously with step 135. After the object is cropped out in step 135c, shown in FIG. 3B, the vertical and horizontal dimensions of the object are derived by using line profiles along the horizontal and vertical directions over the object.

The attenuation of the object is calculated, as if the object was comprised of a high-Z material, in step 150, using an assumption that the thickness of the object is similar to other dimensions, namely the object's horizontal and vertical dimensions that are measurable in the image. The resultant calculated attenuation derived from step 150 is then compared, in step 155, to the net attenuation described with respect to FIG. 3B and shown as image 360. The comparison results in an element in the feature vector used for further decision analysis.

The outcome of the filtering is thus a set of elements that comprise a feature vector for each of the suspicious objects or areas segmented in the radiographic image. The elements in the base feature vector comprise maximum attenuation, net attenuation, the ratio of the attenuation to the area of the suspicious object and the gradient of the suspicious object along the boundary, and the difference produced between the net attenuation and the calculated attenuation. The resulting feature vectors for each potential high-Z area are then evaluated against established decision-making rules, in step 160, to determine whether a high-Z object is present and to render a "Clear" or "High-Z" decision.

It should be appreciated that, if at any programmatic step, no image areas are found to satisfy the image segmentation, geometric-based filters, or characterization analyses, the inspection process can be stopped and the cargo can be deemed inspected and cleared.

Figure 3C:
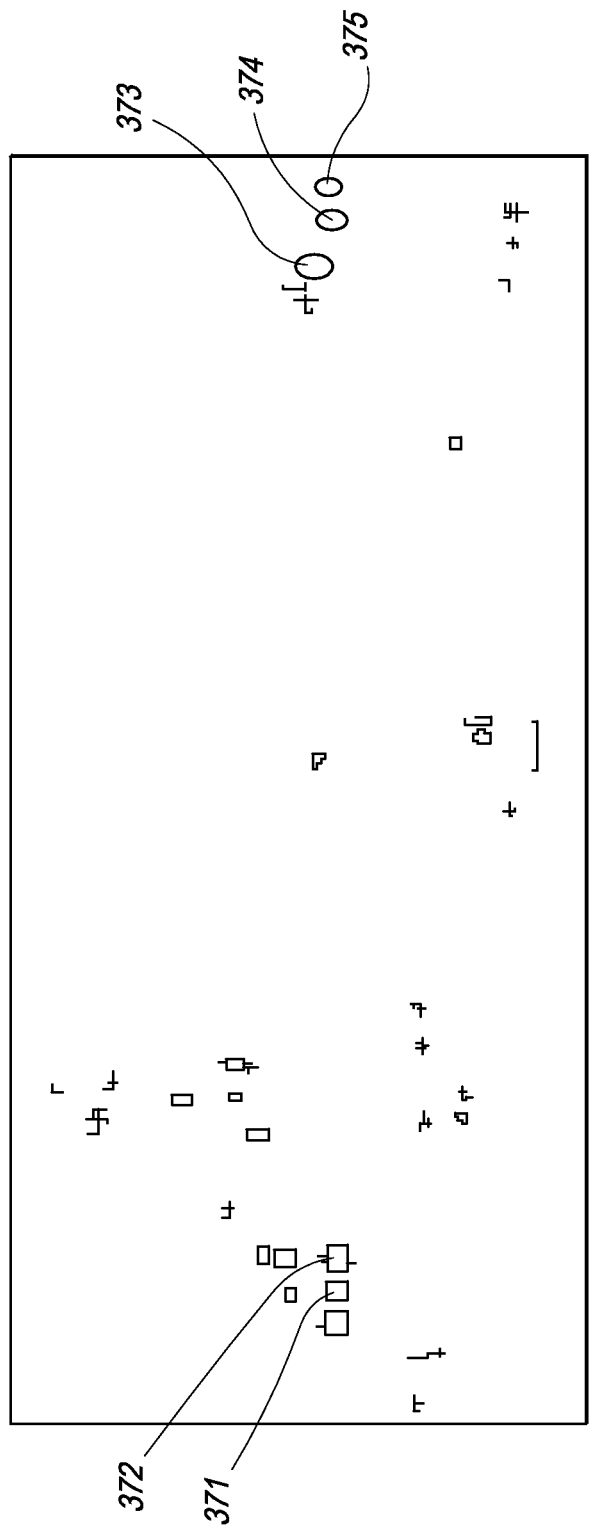
FIG. 3C is an illustration of five objects of interest for further feature vector analysis, using the present invention.

FIG. 3C is a representative example of a subset of the resulting feature vectors and a set of decision-making rules. In one embodiment, the feature vectors shown in FIG. 3C derived by the characterization module as discussed above, are only for those regions segmented from the geometric-based module. As shown in FIG. 3C, five listed objects 371, 372, 373, 374, and 375 are sent to the decision analysis module, with their feature vectors. FIG. 3D is a representative feature vector table, where V1 is maximum attenuation, V2 is net attenuation, V3 is the ratio of the maximum net attenuation to area, and V4 is the vertical gradient, with values for each of objects 371, 372, 373, 374, and 375, shown in FIG. 3C. In one embodiment, the following is representative of a typical rule for an inspection system based on attenuation, where the maximum attenuation is equivalent to 25,000. The decision analysis is used to determine whether the system should alarm indicating a threat condition:

```
If V1 ≤ 24,500, then If V2 > 5000 AND V3 > 50 AND V4 > 600,
THEN
    ALARM
Else
    CLEAR
End
Else
    SEND to Saturation Procedure
End
```

When the "if conditions" are met, i.e., V1 is less than it preset value and all of the remaining feature vector elements exceed preset values, the methods of the present invention are programmed to identify that object as high-Z and subsequently draw a red box labeled "High-Z" around the object in the radiographic image.

As a result, in the example provided, objects 373, 374, and 375 will alarm as potential threat items. The precise numerical values contained in this rule can be adjusted to achieve a given probability of detection and false alarm rate. Additionally, similar rules can be developed for systems that rely on transmission and for systems with different scales for the maximum attenuation or transmission.

Figure 4:
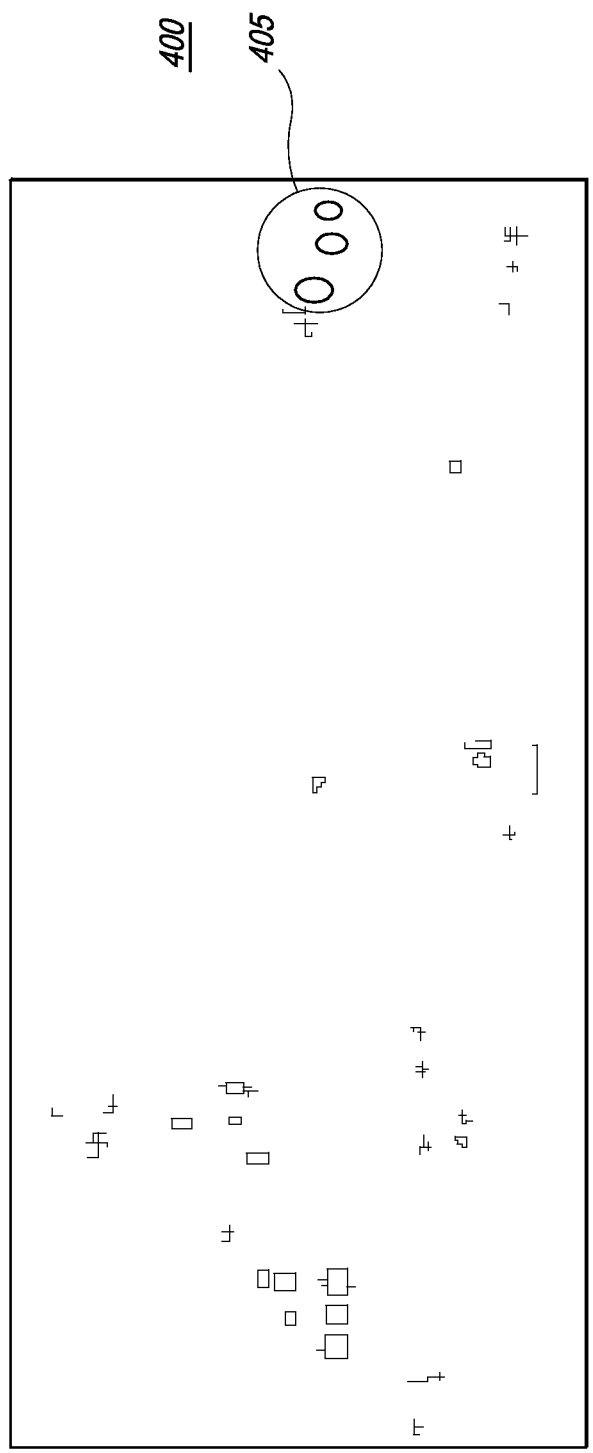
FIG. 4 is a depiction of suspicious objects or areas derived from the method of the present invention for automatically and rapidly detecting the presence of high-Z materials.

FIG. 4 is a final map of suspicious objects or areas, binary image 400, derived from the methods of the present invention for automatically and rapidly detecting the presence of high-atomic-number (high-Z) materials described above. Binary image 400 results from the decision analysis and includes three highlighted regions 405 that represent potential high-Z alarms.

Figure 5:
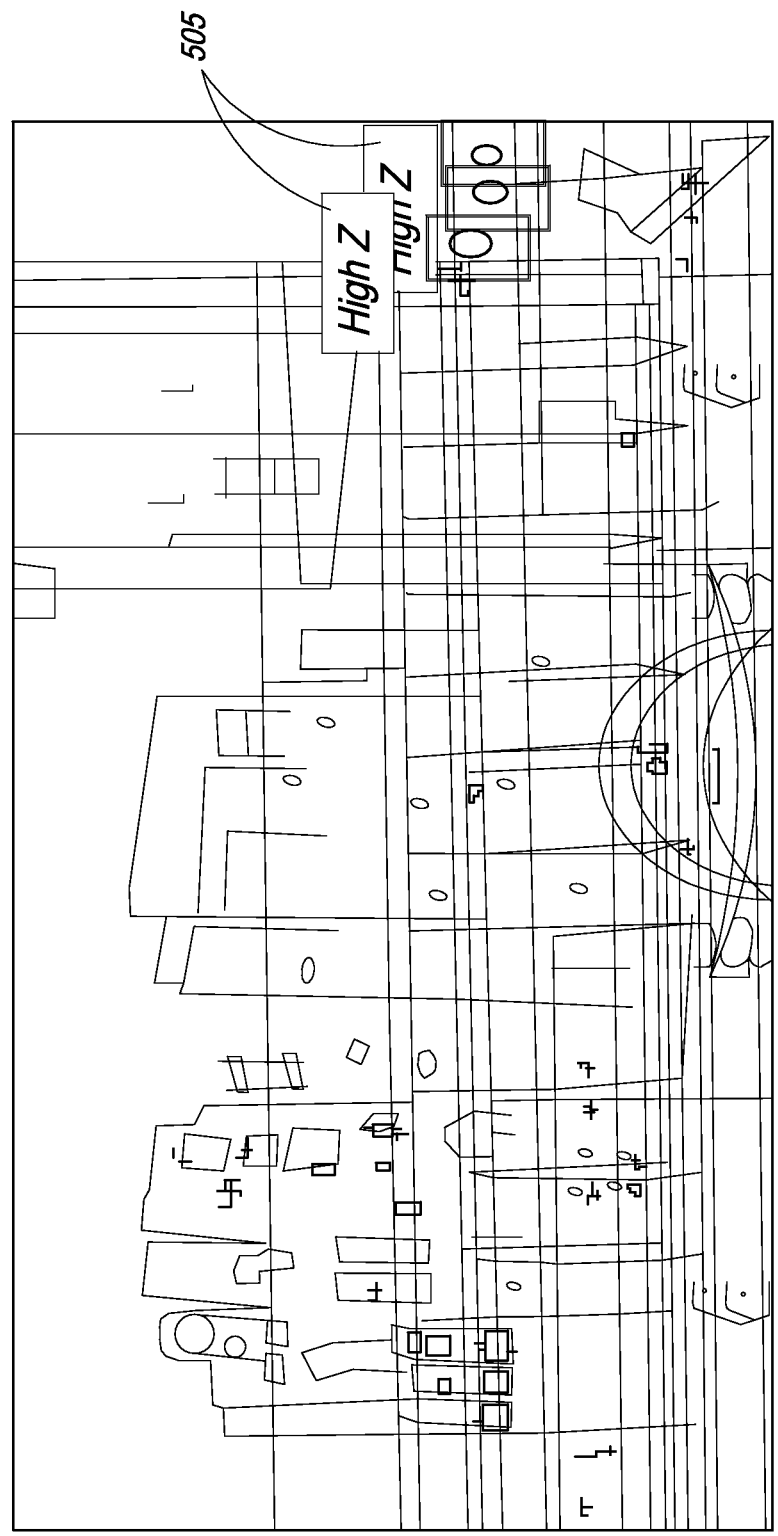
FIG. 5 is an illustration of an X-ray radiographic image of a cargo container after analysis using the methods of the present invention for automatically and rapidly detecting the presence of high-Z materials.

These three highlighted regions are then used to identify the high-Z alarm regions in the radiographic image using boxes 505 shown in FIG. 5. Thus, FIG. 5 is a radiographic image of a cargo container after analysis using the methods of the present invention for automatically and rapidly detecting the presence of high-atomic-number (high-Z) materials.

In one embodiment, the high-Z detection methods of the present invention are capable of using signal analysis techniques to analyze partially saturated regions and, subsequently, group pixels based on their spatial correlations and noise frequency patterns.

Partial penetration or partial saturation occurs when an object itself has sufficiently high attenuation or is superimposed on heavily attenuating materials, such as thick steel plates, as shown in FIGS. 6A AND 6B. FIG. 6A is a radiographic image, showing high-Z objects hidden behind 15 inches of steel. As can be seen in FIG. 6A, in radiographic image 600, some pixels are saturated and observable as black-colored regions 605. Once saturation is reached, estimating the net attenuation becomes challenging as these saturated regions have the same maximum pixel values. The distribution of black pixels is different between the circular objects (low frequency) and the area above them (high frequency), which is due to the attenuation of the 15-inch steel plates. Persons of ordinary skill in the art would appreciate that while it is possible for human vision to discern this pattern difference, it is challenging for automatic methods on computers to identify these areas as separate objects.

Thus, in order to estimate the attenuation values in partially saturated cases, a noise reduction step 127 is performed. The noise reduction step is similar to the segmentation step 110 of FIG. 1, described previously to generate a map of suspicious areas for further processing. Once the objects are segmented out, in an analogous fashion to the segmentation step described with respect to FIG. 1, a noise-reduction technique, such as the use of wavelets, well known to persons of ordinary skill in the art is applied to both the object and the background. The noise reduction technique is applied by using a processor that loads from a memory device (hard disk, RAM, ROM, RAID array, flash drive, USB device, or other memory) the data representative of the segmented images of the radiographic image and that subjects the data to a program which performs noise-reduction calculations as known to persons of ordinary skill in the art.

For these partially saturated cases, it is possible to estimate the attenuation values after the noise reduction step 127. It should be noted that noise reduction is a necessary step for partially saturated cases, and is performed after segmentation and prior to the physics-based characterization step. The estimated attenuation values, along with other features, such as background attenuation, the percentage of the saturated pixels within an object, and object sizes, are fed into the detection decision rules for classification. In an optional embodiment, once the segmentation and noise reduction steps are performed, objects or areas containing a high-Z material (i.e., tungsten) hidden behind shielding materials are highlighted. In one embodiment, the objects or areas containing high-X materials are highlighted by drawing a box around the suspicious area.

Insufficient penetration occurs when the attenuation of the X-ray beam by the material in the cargo is greater than the dynamic range of the X-ray imaging system. In these areas, the image is completely saturated and dominated by image noise. Therefore, the object cannot be differentiated from the background. In such cases, the threat detection methods of the present invention segments these areas and labels them, such as by highlighting the areas or drawing a box around them, to indicate that they are saturated in the radiographic image.

Figure 6:
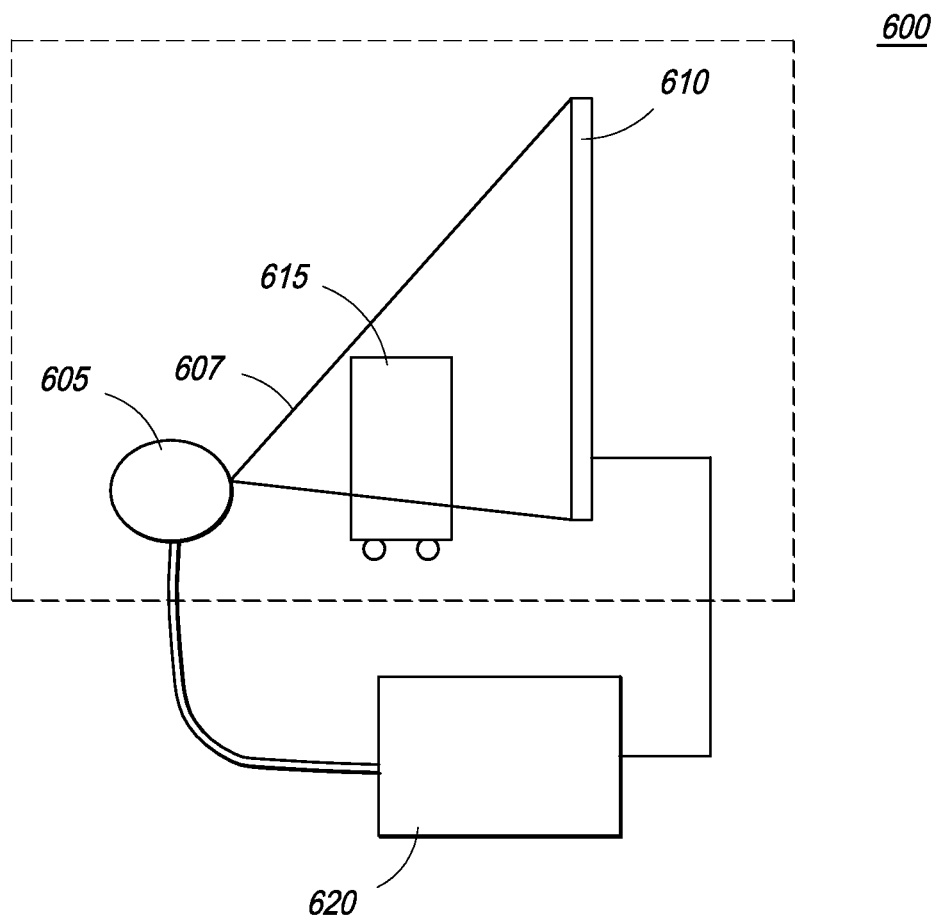
FIG. 6 is a representative diagram of one embodiment of the method of the present invention integrated with a conventional X-ray transmission cargo container screening system.

In one embodiment, the threat detection methods of the present invention are implemented as software installed and executed on a computer associated with a radiographic threat detection system. In one embodiment, the radiographic threat detection system is a cargo scanning system. FIG. 6 is a diagrammatic illustration showing the use of a cargo X-ray scanning system 600, comprising X-ray source 605 and transmission detectors 610. The attenuated X-ray beam 607 is captured by detectors 610 after transmission through the cargo container 615. The detector signals are then digitized and presented as a radiographic image (not shown) on a display or monitor on computing system 620. The computing system 620 comprises the software application of the present invention that uses the initial radiographic image as its input to automatically detect and determine high-Z objects, as described with respect to FIG. 1.

The methods of the present invention can be used with all imaging system configurations regardless of the approach employed to create the relative motion between the radiation source and the object being inspected. These imaging system configurations include, but are not limited to, portal (i.e. drive-through); mobile (e.g. imaging systems on trucks, straddle carriers, etc.); gantry (i.e. moves along rails or tracks); and, car wash (employ vehicle transport systems to move vehicles through an X-ray building or tunnel).

In one embodiment, system 600 is a high-energy penetrating X-ray system, such as one that employs a linear accelerator X-ray source with accelerating potential in the millions of volts (MV). In one example, the high-Z detection methods of the present invention are implemented on Rapiscan Systems' 6 MV Eagle™ Portal cargo inspection system and is directly extended to Rapiscan Systems' Eagle™ Classic and Eagle™ Gantry systems which employ the same 6 MV imaging system. In addition, the high-Z detection methods of the present invention is also ported to Rapiscan Systems' 4.5 MV line of inspection systems, which includes the Eagle Mobile, as well as Rapiscan System's 4.5 MV Portal and Gantry systems that use similar X-ray imaging systems. Furthermore, the high-Z detection methods of the present invention are also implemented with Rapiscan Systems' 9 MV Portal, Gantry, or Mobile systems.

The high-Z detection methods of the present invention can also be implemented in dual-energy cargo inspection systems that include X-ray sources above approximately 3 MV. The present invention is directed towards methods for detecting specific classes of materials (i.e. high-Z) within radiographic images, notwithstanding the method used to obtain the images or the energy of the X-ray or gamma-ray source that is employed. Similarly, the high-Z detection methods of the present invention can be employed with other technologies and embodiments of inspecting cargo.

In an alternate embodiment, an object under inspection is scanned twice, albeit at different angles, if a first scan indicates the presence of a high-Z item in an object under inspection. The methods of the present invention can, in some cases, generate an alarm due to random superposition of materials along the radiation path length. In one embodiment, data are collected for two or more views, such that the alarm can be resolved and false positives are further eliminated.

Referring back to FIG. 6, in one embodiment, in a first step, the X-ray beam 607 scans the container 615 at a first angle relative to the direction of motion of the object under inspection, which is the container 615. In one embodiment, the first scanning angle is 90 degrees. The X-ray source 605 and detectors 610 are then aligned at a second angle (which is, in one embodiment, different from the first scanning angle) relative to the direction of motion of the container 615 and a second scan is subsequently obtained. Thereafter, a "Clear" or "High-Z" decision is rendered by the method of the present invention by analyzing both first and second radiographic scan images, taken at different angles. Thus, if both images confirm the presence of a high-Z object, an alarm is rendered.

In one configuration, the X-ray scanning system 600 is mounted on a mobile inspection vehicle so that the second scan is generated by moving the inspection vehicle relative to the container 615. In another configuration, the X-ray scanning system 600 is mounted on a gantry and the second scan is generated by moving the gantry relative to the container 615.

In another embodiment, the X-ray scanning system 600 comprises two detector arrays positioned at an angle relative to one another. For example, the two detector arrays, in one embodiment, form a 10-degree angle relative to one another. In this embodiment, the X-ray source 605 irradiates the container 615 causing the two detectors to capture attenuated X-ray signals at different positions. Thereafter, a "Clear" or "High-Z" decision is rendered by the present invention by analyzing signals from both detector arrays.

In one embodiment, the X-ray scanning system 600, modified with the use of two detector arrays angled relative to one another, is mounted on a mobile inspection vehicle.

In a second embodiment, scanning system 600, comprising two detector arrays at an angle relative to one another, is mounted on a gantry.

In a third embodiment, scanning system 600, comprising two detector arrays at an angle relative to one another, has a collimator at its source 605 that restricts the X-ray beam 607 while irradiating the two detector arrays. The collimator, in one embodiment, is designed to enable one X-ray source to produce two narrow X-ray beams, separated by an angle; the collimator blocks the remainder of X rays from the emitting source. The advantage of this configuration is that two views can be obtained simultaneously, obviating the need (and the time) for a second scan.

In a yet another embodiment, X-ray scanning system 600 completes a first scan with the X-ray beam 607 at a first angle relative to the direction of motion of the container 615. In one embodiment, the first scan angle is 90 degrees. If the automated threat detection method of the present invention detects at least one threat object in the first scan image, a second scan is conducted with the X-ray source 605 raised or lowered to obtain an image at a second scan angle, where the second scan angle is different from the first scan angle, and is relative to the direction of motion of the container 615 and the detectors 610. Thereafter, a "Clear" or "High-Z" decision is rendered by the method of the present invention by analyzing both radiographic scan images from the first scan and second scan, taken at different angles. For example, if both images confirm the presence of a high-Z object, an alarm is rendered.

Persons of ordinary skill in the art would appreciate that the aforementioned dual-angle scan systems enable further reduction of false alarm rates when used with the high-Z detection method of the present invention without substantially compromising on system throughput and cost.

The high-Z detection methods of the present invention can be used to enhance the performance of both dual- and multi-energy cargo inspection systems as well. First, the method described above with respect to FIG. 1 can be applied to a high-energy radiographic image to provide an analysis of the image that is orthogonal to the dual-energy determination of the effective-Z of the material. This will help alleviate some of the limitations of dual-energy imaging. Specifically, one limitation for large cargo containers is that due to the effect of overlapping materials having different densities and atomic numbers, the result may be an inaccurate estimate of the effective Z. Additionally, the low-energy beam typically has a lower intensity and penetration than the high-energy beam. Thus, the low-energy image can become saturated due to the low-energy beam being heavily attenuated by the cargo. As a result, the signal-to-noise ratio is low and the dual-energy process cannot be successfully employed. In such cases, the high-Z detection methods of this invention will continue to operate on the high-energy image, thus extending the range of penetration that the dual-energy cargo inspection system can use to detect high-Z materials.

Figure 7:
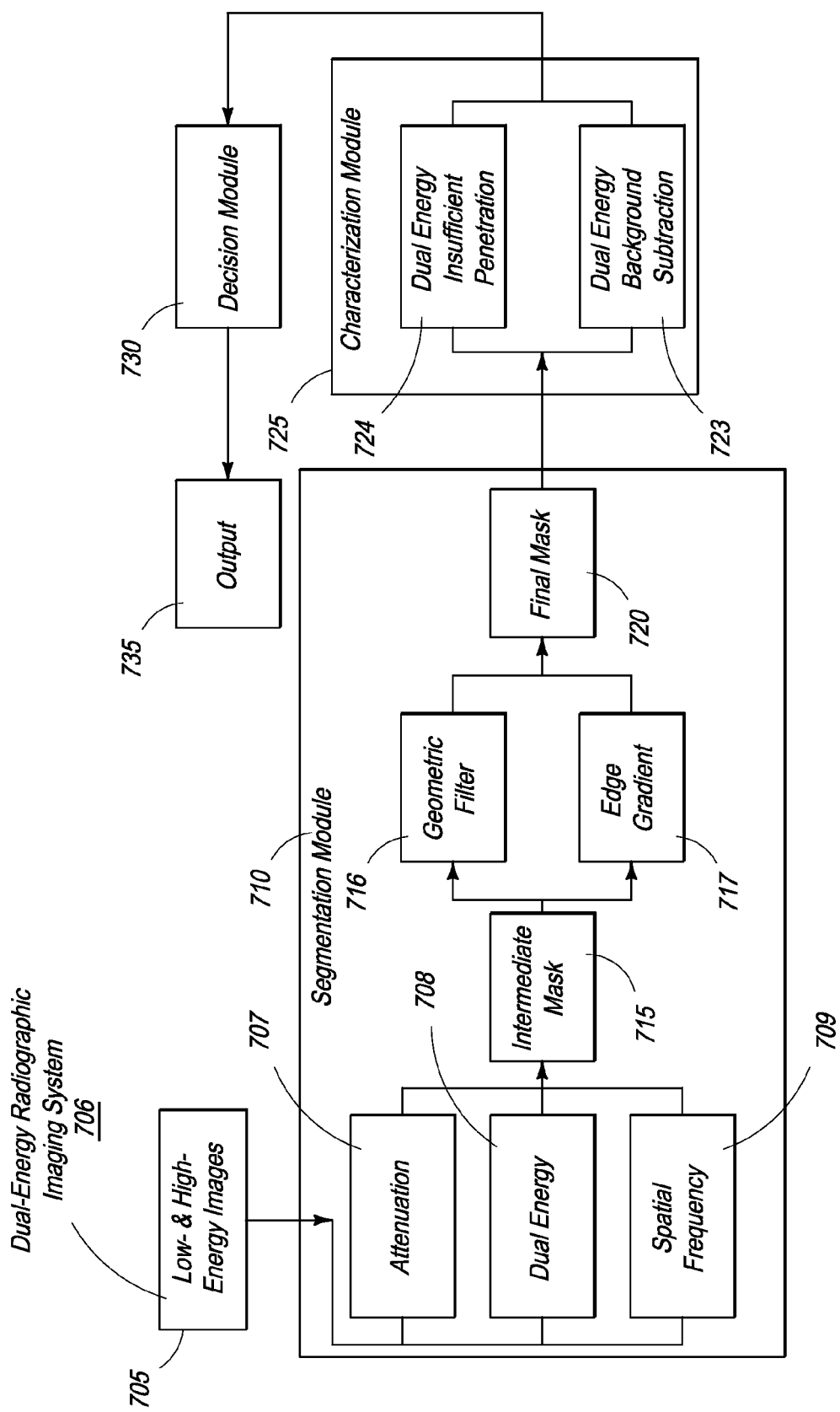
FIG. 7 is a block diagram illustrating steps of one embodiment of a dual-energy radiographic imaging method of the present invention for automatically and rapidly detecting the presence of high-Z materials.

Secondly, the high-Z detection methods of the present invention can be applied to the additional information provided by dual-energy imaging below the penetration limit of the low-energy image. FIG. 7 is a block diagram illustrating the steps of the dual-energy-based automatic high-Z detection methods of the present invention. In one embodiment, the dual-energy-based high-Z detection methods of the present invention, in step 705, receives two radiographic images from a dual-energy X-ray imaging system 706, a low-energy image and a high-energy image.

Both the low-energy and the high-energy radiographic images 705 serve as input to the dual-energy-based high-Z detection methods of the present invention. The images are subsequently processed within segmentation module 710. Within the attenuation segmentation block, in step 707, both low-energy and high-energy images are pre-processed using the same approach described in step 110 of FIG. 1, through the following two separate attenuation criteria, to determine regions that potentially contain high-Z objects:

$$\Sigma\mu L \geq A_{low} \text{ and} \qquad \text{EQUATION 2:}$$

$$\Sigma\mu L \geq A_{high} \qquad \text{EQUATION 3:}$$

where L is thickness and $\mu$ is the linear attenuation coefficient of the object under inspection and $A_{low}$ and $A_{high}$ are predetermined attenuation values in the low-energy and high-energy images, respectively. Persons of ordinary skill in the art should note that since there is a difference in penetration power between the low-energy and high-energy X rays, the two aforementioned criteria, that process the information separately, provide potentially useful information in terms of the insufficient penetration region, among other characteristic information. A similar rule can be developed based on the transmission of X rays.

In step 708, the dual-energy segmentation block processes the ratio of the pre-processed images with the following criterion, to calculate effective-Z of the potential high-Z regions:

$$\Sigma\mu(E_{high})/\Sigma\mu(E_{low}) \geq T_{low\text{-}high} \qquad \text{EQUATION 4:}$$

Where $\mu(E_{high})$ and $\mu(E_{low})$ are the absorption coefficients estimated at the high- and low-energy images and the $T_{low\text{-}high}$ is a predetermined value related to the effective Z of the object and surrounding materials. It should be appreciated by those of ordinary skill in the art that although the aforementioned ratio, $T_{low\text{-}high}$, contains the contributions from all the materials along the X-ray path, the ratio is independent from that obtained by using attenuation criteria in Equation 2 and 3. The dual-energy segmentation step 708 indicates a different physical quantity, which has no object depth (L) dependence.

In one embodiment, the dual-energy information ratio is empirically determined from a series of radiographic calibration images, which are comprised of various combinations of high-, medium- and low-Z objects and thicknesses of high-, medium- and low-Z overlapping materials. This process helps compensate for situations found in low attenuation and contrast images, where the high-Z objects and neighboring cargo having similar attenuation values.

In step 709 of processing spatial frequencies, anomalies that have characteristics different from the surrounding cargo are detected using a low-pass filter such as the Gabor wavelet. For example, using Gabor wavelet the filtering criterion is the absolute value of Gabor filtered region:

$$|G(x,y,\theta) * I(x,y)| \geq T_G \qquad \text{EQUATION 5:}$$

where $G(x,y,\theta)$ and $I(x,y)$ are the Gabor filter and the high-energy attenuation or transmission image, respectively, and $T_G$ is a threshold that is pre-determined or dynamically set during the filtering process. The advantageous properties of the Gabor wavelet are its sensitivity to local spatial frequency and the invariance in angular and scaling space due to the band of functions covering scaling and angular space for a given frequency range. Other characteristic filters can also be employed.

The image segmentation is performed by using a processor that loads from a memory device (hard disk, RAM, ROM, RAID array, flash drive, USB device, or other memory) the data representative of the two radiographic images and that subjects the data to a program which performs the image segmentation calculations as described herein.

The image segmentation module 710 at this stage generates an intermediate image mask 715 of the segmented low-energy and high-energy radiographic images that is further subjected to a set of geometrical filters and a gradient edge filter, at steps 716 and 717 respectively, aiming at the relatively low-attenuation threat objects embedded in a highly cluttered cargo. Steps 716 and 717 are similar to those already described with reference to step 110 and block 111 of FIG. 1 of the present invention and will not be discussed herein Subsequently, the resultant final image mask 720, comprising at least one suspicious area, is passed onto the characterization module 725. The characterization module 725 analyzes each region within the image map 720 and generates a feature matrix, which includes outputs of a plurality of functions within the characterization module 725—as have been earlier described with reference to the single-energy methods of FIG. 1. However, the dual-energy-based threat detection methods of the present invention differ in the sense that to further improve Z estimation, the contribution to the effective-Z due to overlapping materials is determined and used to estimate, in step 723, the net effective-Z of the potential high-Z object. Additionally, in step 724, if it is determined that there is too low a signal-to-noise ratio (SNR) with reference to the low-energy image data, only the high-energy image data are used to render a decision on high-Z threats using the steps shown in FIG. 1.

Subsequently, the resulting feature vectors for each potential high-Z area, combining the results of performing the steps in FIG. 1 and FIG. 7, are evaluated against established decision-making rules, by the decision block 730, to determine whether a high-Z object is present and to render a "clear" or "high-Z" decision 735. It should be noted herein that while the decision-making methods of this embodiment are similar to that of the single-energy case, specific rules are implemented to deal with feature vectors from dual-energy data.

While the present invention describes methods employing dual-energy radiography, the methods are extensible to other radiographic methods, such as those employing multiple energies and dual-species radiography where both neutrons and X rays or gamma rays are employed. It should be appreciated that the present invention has been described in accordance with multiple different embodiments. Other features, functions, or structures which are equivalent to the ones disclosed herein or obvious alternatives to a person of ordinary skill in the art are intended to be part of, and encompassed by, the present invention.

The invention claimed is:

1. A method of processing radiographic image data of an object, comprising:
   activating a radiation source;
   using a detector array, detecting radiation emitted from the radiation source and passing through an inspection volume and the object to generate data representative of a radiographic image;
   using a processor, processing said data representative of the radiographic image by generating a first map, using areas on said first map to generate a mask, and electronically cropping out portions of the radiographic image to yield a second map that highlights regions representative of potential threats, wherein the first map is generated by performing image segmentation, wherein said image segmentation is performed by determining local maximum attenuation values or minimum attenuation values of the radiographic image, and wherein a plurality of geometric filters is applied to the first map.

2. The method of processing radiographic image data of claim 1 further comprising performing image segmentation by employing edge gradients to identify potential high atomic number areas.

3. The method of processing radiographic image data of claim 2 wherein the plurality of geometric filters are defined in terms of shape, symmetry, size and homogeneity.

4. The method of processing radiographic image data of claim 1 wherein one of said plurality of geometric filters is a size filter and wherein said size filter is configured to exclude image regions that are smaller than a minimum size of objects to be detected.

5. The method of processing radiographic image data of claim 1 wherein one of said plurality of geometric filters is a size filter and wherein said size filter is configured to exclude image regions that are larger than a size of an object through which a penetration of the radiation emitted from the radiation source becomes insufficient.

6. The method of processing radiographic image data of claim 1 wherein one of said plurality of geometric filters is a size filter and wherein the size filter is configured to filter at least one area to identify dimensions selected on a basis of spatial resolution or radiation penetration.

7. The method of processing radiographic image data of claim 1 wherein one of said plurality of geometric filters is a shape filter and wherein said shape filter is configured to exclude image regions of an object with an aspect ratio greater than a pre-determined value and not exclude image regions with primitive shapes.

8. The method of processing radiographic image data of claim 7 wherein the primitive shapes is at least one of a cube, cylinder and sphere.

9. The method of processing radiographic image data of claim 7 wherein the pre-determined value is between 4 and 20 and wherein the aspect ratio is derived by calculating a ratio of a length of a major axis to a length of a minor axis of the object.

10. The method of processing radiographic image data of claim 1 wherein one of said plurality of geometric filters is a symmetry filter and wherein said symmetry filter is configured to characterize a two-dimensional boundary of the radiographic image as a one-dimensional function of a polar angle from a centroid of the radiographic image.

11. The method of processing radiographic image data of claim 1 wherein one of said plurality of geometric filters is a homogeneity filter and wherein the homogeneity filter is defined by a ratio of a number of pixels in an area of the radiographic image to a number of pixels contained in a bounding box around said area of the radiographic image.

12. The method of processing radiographic image data of claim 10 wherein said ratio is between 40 and 80.

13. The method of processing radiographic image data of claim 1 wherein the plurality of geometric filters comprise a shape filter, a symmetry filter, a size filter and a homogeneity filter and wherein each of said shape filter, symmetry filter, size filter and homogeneity filter are applied to the radiographic image serially.

14. The method of processing radiographic image data of claim 1 wherein the plurality of geometric filters comprise a shape filter, a symmetry filter, a size filter and a homogeneity filter and wherein each of said shape filter, symmetry filter, size filter and homogeneity filter are applied to the radiographic image in parallel.

15. The method of processing radiographic image data of claim 1 further comprising applying a plurality of feature vectors to said regions representative of potential threats.

16. The method of processing radiographic image data of claim 15 wherein said plurality of feature vectors comprise at least one of maximum attenuation, net attenuation, a ratio of attenuation to an area of a suspicious object, a gradient of a suspicious object along a boundary, and a difference produced between measured background corrected attenuation and calculated attenuation.

\* \* \* \* \*